United States Patent [19]

Narandja et al.

[11] Patent Number: 5,688,924

[45] Date of Patent: Nov. 18, 1997

[54] DERIVATIVES OF 12,13-EPOXY-TYLOSIN AND PROCESSES OF MANUFACTURE THEREOF

[75] Inventors: Amalija Narandja; Nevenka Lopotar, both of Zagreb, Croatia

[73] Assignee: PLIVA farmaceutska, kemijska, prehrambena i kozmeticka industrija, d.d., Zagreb, Croatia

[21] Appl. No.: 696,178

[22] Filed: Aug. 13, 1996

[30] Foreign Application Priority Data

Aug. 14, 1995 [HR] Croatia ................................. 950449

[51] Int. Cl.$^6$ ........................... C07D 313/00; C07H 5/06; C07H 17/08
[52] U.S. Cl. .............................. 536/7.1; 549/270
[58] Field of Search ..................... 549/270; 514/30; 536/7.1

[56] References Cited

U.S. PATENT DOCUMENTS 4,808,575  2/1989  Mallams et al. .......................... 514/30

*Primary Examiner*—Bernard Dentz
*Attorney, Agent, or Firm*—Pollock, Vande Sande & Priddy

[57] ABSTRACT

The invention relates to derivatives of 12,13-epoxy-tylosin, the novel semisynthetic antibiotics from tylosin group and the methods of their preparation. According to this invention hydrogenation followed by oximation of 12,13-epoxy-tylosin derivatives yields the following tylosin derivatives: 10,11-dihydro-12,13-epoxy, respectively 10,11-dihydro-12,13-epoxy oxime.

Direct oximation of 12,13-epoxy tylosin derivative gives 12,13-epoxy oxime derivatives of tylosin.

18 Claims, No Drawings

DERIVATIVES OF 12,13-EPOXY-TYLOSIN AND PROCESSES OF MANUFACTURE THEREOF

TECHNICAL PROBLEM

The present invention relates to tylosin derivatives, novel synthetic products from macrolide class exhibiting antimicrobial activity. More specifically, the invention relates to 12,13-epoxy-tylosin derivatives of the formula I

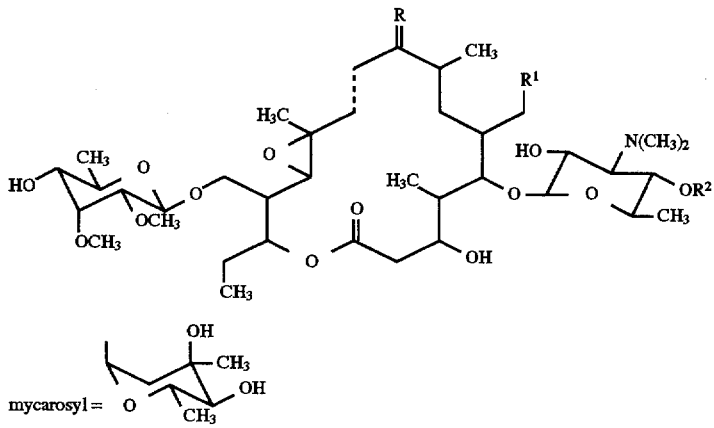

I wherein R stands for O, $R^1$ stands for CHO or $CH(OCH_3)_2$, $R^2$ stands for H or mycarosyl, and — has the meaning of a single bond;

wherein R stands for NOH, $R^1$ stands for CHO or $CH(OCH_3)_2$, $R^2$ stands for H or mycarosyl and — has the meaning of a single or a double bond;
and to the compounds of the formula II

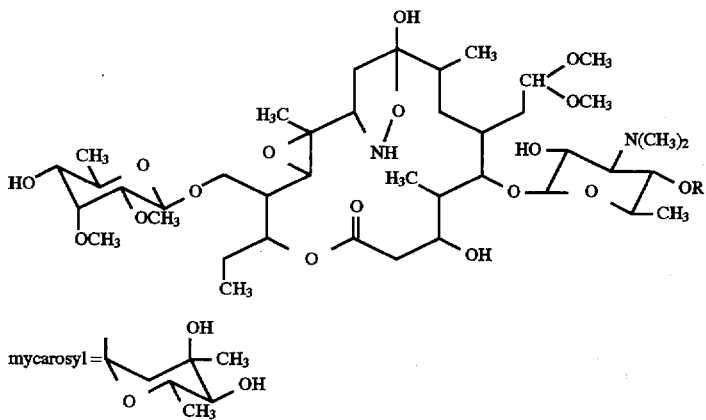

II wherein R stands for H or mycarosyl and to processes for preparation of said compounds.

PRIOR ART

A series of modifications on the diene part of the 16-membered tylosin ring was performed. It is known that addition of thiols gave 11-thioethers of tylosin (S. Omura U.S. Pat. No. 4,594,338). It is also known that by catalytic hydrogenation of diene and oximation in position C-9 and C-20 tylosin 10,11,12,13-terahydro derivatives were prepared, their oximes respectively (A. Naranda U.S. Pat. No. 5,023,240).

It is known that the selective oxidation of tylosin gave 12,13-epoxy derivatives (A. K. Mallams U.S. Pat. No. 4,808,575). Also dihydro and tetrahydro derivatives of other 16-membered macrolides with 12,13-epoxy structure were prepared. It is also known that catalytic hydrogenation of maridomycin gave 13-hydroxy-10,11,12,13-tetrahydro maridomycin (M. Muroi, Chem.Pharm.Bull. 24, (1976) 450), where the reduction of C10–C11 double bond was accompanied with opening of oxirane ring, while catalytic hydrogenation of rosamycin gave 10,11-dihydro derivative with preserved 12,13-epoxy structure. It is also known that C-20 aldoximes were prepared by oximation of rosamycin and its 12,13-de-epoxy derivative (H. Reinmann U.S. Pat. No. 4,056,616).

In the hitherto known prior art 10,11-dihydro derivatives of 12,13-epoxy tylosin and their C-9 oximes, 12,13-epoxy-tylosin oximes as well as 10,11-dihydro-12,13-epoxy compounds with 9,11-epoxyimino bridge are not being described, and neither are the processes for preparation of tylosin derivatives mentioned herein.

DESCRIPTION WITH WORKING EMBODIMENTS

It was found that derivatives of 12,13-epoxy-tylosin of the formula I

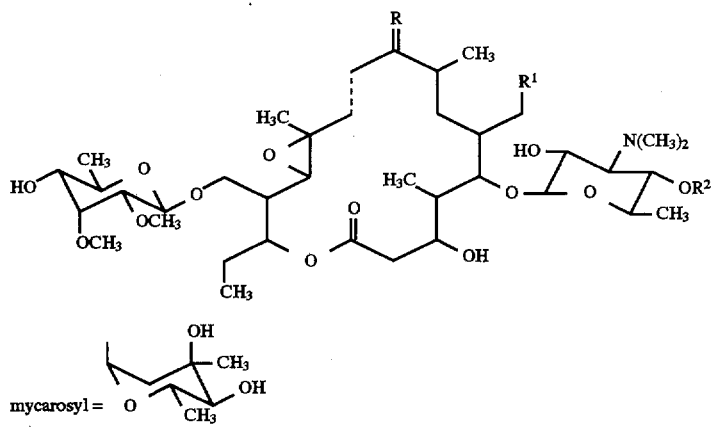

I wherein R stands for O, $R^1$ stands for CHO or $CH(OCH_3)_2$, $R^2$ stands for H or mycarosyl and — has the meaning of a single bond wherein R stands for NOH, $R^1$ stands for CHO or $CH(OCH_3)_2$, $R^2$ stands for H or mycarosyl, and — has the meaning of a single or a double bond and the compounds of the formula II

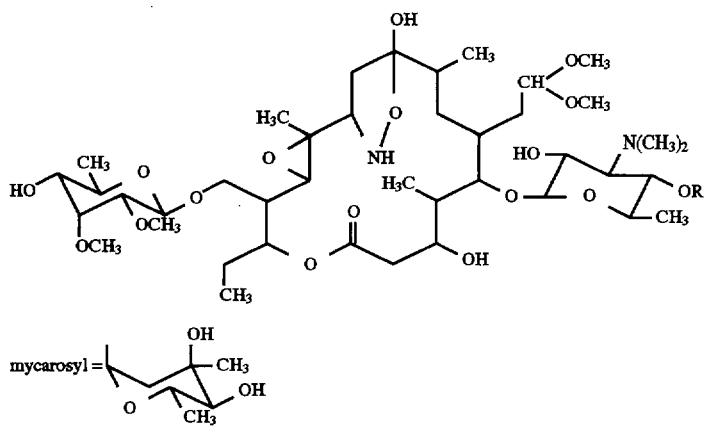

II wherein R stands for H or mycarosyl, could be prepared in such a way that the compound of the formula III

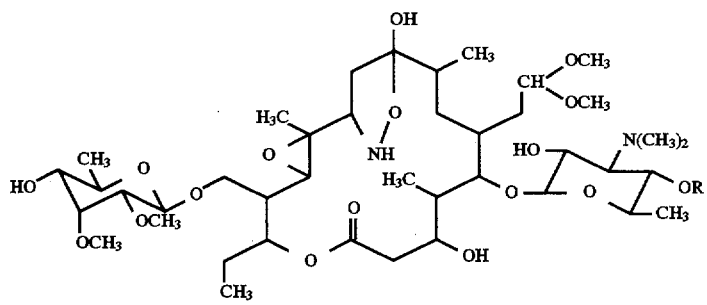

II

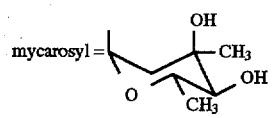

A/ wherein R stands for CHO or CH(OCH$_3$)$_2$, R$^1$ stands for H or mycarosyl and R$^2$ stands for N(CH$_3$)$_2$ or N—O(CH$_3$)$_2$ when R$^1$ stands for H;

is subjected to hydrogenation in an organic solvent, primarily a lower C$_1$–C$_3$ aliphatic alcohol with 2–5% w/w palladium-on-charcoal and hydrogen pressure of 0.2–0.5 MPa at ambient temperature for 5–8 hours and then optionally the obtained compound of the formula I wherein R stands for O, R$^1$ stands for CH(OCH$_3$)$_2$, R$^2$ stands for H or mycarosyl, and — has the meaning of a single bond is subjected to oximation with 3–6 equivalent hydroxylamin hydrochloride in pyridine or a lower alcohol with the addition of the base, such as pyridine (or Na$_2$CO$_3$), in nitrogen stream at room temperature or reflux temperature for 3–7 hours, and then optionally to hydrolysis of acetal group in the mixture of acetonitrile and 0.2N HCl (1:1) or the mixture of acetonitrile and 1% trifluoroacetic acid in water (1:2) at ambient temperature for 2 hours;

B/ wherein R stands for CH(OCH$_3$)$_2$, R$^1$ stands for H or mycarosyl and R$^2$ stands for N(CH$_3$)$_2$ is subjected to oximation reaction as described above, and the products obtained:

the compound of the formula I wherein R stands for NOH, R$^1$ stands for CH(OCH$_3$)$_2$, R$^2$ stands for H or mycarosyl and — has the meaning of a double bond, and the compound of the formula II, wherein R stands for H or mycarosyl are chromatographically separated on a silicagel column and optionally subjected to acetal group hydrolysis in the described way.

In this invention the new compounds are isolated by conventional extraction with halogenated carbohydrates such as carbon tetrachloride, chloroform or methylene chloride from aqueous alkaline solutions and the evaporation to a dry residue.

If necessary, separation of reaction products or purification for spectral analysis are performed on silicagel column (Silicagel 60 Merck Co., 230–400 mesh/ASTH, 60–230 mesh/ASTH respectively) in the solvent system: methylene chloride—methanol—ammonium hydroxide; A (90:9:1.5) or B (90:9:0.5).

Identification of novel compounds was made by UV and NMR spectroscopy.

The novel compounds show an antibacterial effect and can be used as intermediates in preparation of new tylosine derivatives.

The invention is illustrated by the following examples not limiting to any extent the scope of the invention.

EXAMPLE 1

10,11-Dihydro-12,13-epoxy tylosin 20-dimethyl acetal (1)

12,13-Epoxy-tylosin 20-dimethyl acetal (2.4 g, 2.4 mmole) is dissolved in 240 ml of ethanol, 10% Pd/C (0.72 g) is added and the mixture is hydrogenated at ambient temperature under hydrogen pressure of 0.2 MPa for 8 hours. With the reaction completed the catalyst is filtration-separated, ethanol is evaporated under reduced pressure to dry product which is then chromatographed on a silicagel column.

Yield: 1.25 g (52%) Rf(A) 0.65

$^1$H-NMR(CDCl$_3$) ppm 5.10 (1H,d,1''), 4.58(1H,d,1'''), 4.24(1H,d,1'), 3.64 (3H,s,3'''OMe), 3.51(3H,s,2'''OMe), 3.39 (3H,s,20-OMe), 3.24(3H,s,20-OMe), 2.52(6H,s,NMe$_2$), 1.34(3H,s,12-CH$_3$);

$^{13}$C-NMR (CDCl$_3$) ppm 212.31 (s,C-9), 170.48(s,C-1), 103.27(d,C-1'), 102.94(d,C-20), 99.36(d,C-1'''), 96.54(d,C-1''), 60.66(q,3'''OMe), 59.28(s ,C-12), 58.30 (q,2'''OMe), 58.27(d,C-13), 53.21(q,20-OMe), 50.43(q,20-OMe), 33.87 (t,C-10), 28.95(t,C-11), 18.36(q,C-22).

EXAMPLE 2

10,11-Dihydro-12,13-epoxy-tylosin (2)

12,13-Epoxy-tylosin (2 g, 2.1 mmole) is dissolved in 200 ml of ethanol, 10% Pd/C (0.4 g) is added and hydrogenated at ambient temperature under hydrogen pressure of 0.4 MPA for 7 hrs. The product is isolated as described in Example 1.

Yield: 0.92 g (46%) Rf(A) 0.54

$^1$H-NMR(CDCl$_3$) ppm 9.67 (1H,s,CHO), 5.09(1H,d,1''), 4.58(1H,d,1'''), 4.25(1H,d,1'), 3.65(3H,s,3'''OMe), 3.50(3H, s,2'''OMe), 2.51(6H,s,NMe$_2$), 1.23(3H,s,12-CH$_3$);

$^{13}$C-NMR(CDCl$_3$) ppm 212.33(s,C-9), 202.86(d,C-20), 170.46(s,C-1), 103.25(d,C-1'), 99.36(d,C-1'''), 96.74(d,C-1''), 60.66(q,3'''OMe), 59.29(s,C-12), 58.37(q,2'''OMe;d,C-13), 33.87(t,C-10), 28.95(t,C-11), 18.36(q,C-22).

EXAMPLE 3

10,11-Dihydro-12,13-epoxy-desmycosin 20-dimethyl acetal (3)

Method A 12,13-Epoxy-desmycosin N-oxide 20-dimethyl acetal (2.5 g, 2.9 mmole) is dissolved in 250 ml of ethanol, 1.25 g of 10% Pd/C is added and hydrogenated at ambient temperature under hydrogen pressure of 0.5 MPa for 7 hrs. The product is isolated as described in Example 1.

Yield: 1.27 g (52%) Rf(A) 0.57

$^1$H-NMR(CDCl$_3$) ppm 4.56(1H,d,1'''), 4.25(1H,d,1'), 3.64 (3H,s,3'''OMe), 3.51(3H,s,2'''OMe), 3.38(3H,s,20-OMe), 3.22 (3H,s,20-OMe), 2.52(6H,s,NMe$_2$), 1.33(3H,s,12-CH$_3$);

$^{13}$C-NMR(CDCl$_3$) ppm 212.31 (s,C-9), 170.25(s,C-1), 103.23(d,C-1'), 102.80(d,C-20), 99.34(d,C-1'''), 60.45(q, 3'''OMe), 59.27(s,C-12), 58.28(q,2'''OMe), 58.23 (d,C-13), 53.25(q,20-OMe), 50.45(q,20-OMe), 33.88(t,C-10), 28.99 (t,C-11), 18.38(q,C-22).

Method B 12,13-Epoxy-desmycosin 20-dimethyl acetal (3 g, 3.6 mmole) is dissolved in 250 ml of ethanol, 0.6 g of 10% Pd/C is added and hydrogenated at ambient temperature under hydrogen pressure of 0.5 MPa for 8 hrs. The product obtained by isolation as described in Example 1 is identical to the product obtained when applying Method A.

EXAMPLE 4

10,11-Dihydro-12,13-epoxy-desmycosin (4)

12,13-Epoxy-desmycosin (2.4 g, 3 mmol) is dissolved in 100 ml of ethanol, 0.72 g of 10% Pd/C is added and hydrogenated at ambient temperature under hydrogen pressure of 0.3 MPa for 8 hrs. Isolation performed as described in Example 1.

Yield: 1.3 g (54%), Rf(A) 0.45

$^1$H-NMR(CDCl$_3$) ppm 9.65(1H,s,CHO), 4.55(1H,d,1'''), 4.24(1H,d,1'), 3.64(3H,s,3'''OMe), 3.51(3H,s,2'''OMe), 2.51 (6H,s,NMe$_2$), 1.34(3H,s,12-CH$_3$);

$^{13}$C-NMR(CDCl$_3$) ppm 212.30(s,C-9), 202.36(d,C-20), 170.27(s,C-1), 103.29(d,C-1'), 99.34(d,C-1'''), 60.47(q, 3'''OMe), 59.28(s,C-12), 58.27(q,2'''OMe;d,C-13), 33.89 (t,C-10), 28.97(t,C-11), 18.37(q,C-22).

EXAMPLE 5

10,11-Dihydro-12,13-epoxy-tylosin oxime 20-dimethyl acetal (5)

Compound 1 (3 g, 3 mmole) is dissolved in 39 ml of pyridine, hydroxylamine hydrochloride (1.25 g, 18 mmole) is added and stirred under nitrogen stream at ambient temperature for 7 hours. Reaction solution is diluted with 150 ml of water, alkalized to pH 9 with 10% NaOH and at reduced pressure evaporated to one third of the volume. Extraction with chloroform is performed (2×60 ml to pH 6, 2×60 ml to pH 9.5). Combined extracts of pH 9.5 are washed with saturated solution of NaHCO$_3$, dried (K$_2$CO$_3$) and evaporated to dry residue.

Yield: 1.83 g (61.3%), Rf(A) 0.45

$^1$H-NMR(DMSO) ppm 10.23(1H,s,9-NOH,) disappears on mixing with D$_2$O; 4.99 (1H,d,1''), 4.45 (1H,d,1'''), 4.22 (1H,d,1'), 3.49 (3H,s,3'''OMe), 3.45 (3H,s,2'''OMe), 3.23 (3H,s,20-OMe), 3.14(3H,s,20-OMe), 2.46 (6H,s,NMe$_2$), 1.25(3H,s,12-CH$_3$);

$^{13}$C-NMR(CDCl$_3$) ppm 173.19(s,C-1), 161.69(s,C-9), 104.17(d,C-1'), 102.06(d,C-20), 100.64(d,C-1'''), 96.65(d,C-1''), 62.30(s,C-12), 61.69(d,C-13), 61.43(q,3'''OMe), 59.09 (q,2'''OMe), 16.32(q,C-22).

EXAMPLE 6

10,11-Dihydro-12,13-epoxy-desmycosin oxime 20-dimethyl acetal (6)

Compound 3 (2 g, 2.4 mmole) is dissolved in 20 ml of methanol, 0.64 g of Na$_2$CO$_3$ is added as well as hydroxylamine hydrochloride (0.84 g, 12.3 mmol) and stirred under nitrogen stream at reflux temperature for 3 hours. Reaction solution is poured into 60 ml of water and isolated by pH gradient extraction as described in Example 5.

Yield: 1.1 g (54%); Rf(A) 0.33

$^1$H-NMR(DMSO) ppm 10.22(1H,s,9-NOH) disappears on mixing with D$_2$O; 4.43 (1H,d,1'''), 4.19(1H,d,1'), 3.47 (3H,s,3'''OMe), 3.43(3H,s,2'''OMe), 3.21 (3H,s,20-OMe), 3.12(3H,s,20-OMe), 2,42(6H,s,NMe$_2$), 1.24(3H,s,12-CH$_3$);

$^{13}$C-NMR(CDCl$_3$) ppm 172.98(s,C-1), 161.62(s,C-9), 103.98(d,C-1'), 102.05(d,C-20), 100.51 (d,C-1'''), 62.27(s, C-12), 61.73(d,C-13), 61.42(q,3'''OMe), 59.09(q,2'''OMe), 16.30(q,C-22).

EXAMPLE 7

10,11-Dihydro-12,13-epoxy-tylosin oxime (7)

10,11-Dihydro-12,13-epoxy-desmycosin oxime (8)

Compound (5) (2 g, 2 mmole) is dissolved in the mixture of 20 ml of acetonitrile and 20 ml of 0.2N HCl and stirred at ambient temperature for 2 hours. Reaction solution is diluted with 20 ml of water, alkalized to pH 9 with NaOH, extracted with chloroform (2×30 ml), dried (K$_2$CO$_3$) and evaporated to dry residue. The crude product is chromatographed on a silicagel column.

Yield: 0.64 g (34%) of compound 7; Rf(B) 0.30

$^1$H-NMR (DMSO) ppm 10.23 (1H,s,9-NOH) disappears on mixing with D$_2$O; 9.67 (1H,s,CHO), 4.95 (1H,d,1''), 4.45 (1H,d,1'''), 4.21 (1H,d,1'), 3.49(3H,s,3'''OMe), 3.45(3H,s, 2'''OMe), 2.47(6H,s,NMe$_2$), 1.25 (3H,s,12-CH$_3$);

$^{13}$C-NMR(CDCl$_3$) ppm 203.11(d,C-20), 173.18(s,C-1), 161.65 (s,C-9), 104.15(d,C-1'), 100.62(d,C-1'''), 96.63(d,C-1''), 62.30(s,C-12), 61.76(d,C-13), 61.42(q,3'''OMe), 59.25 (q,2'''OMe), 16.46(q,C-22); and 0.35 g (23%) of compound 8; Rf(B) 0.22

$^1$H-NMR(DMSO) ppm 10.21(1H,s,9-NOH) disappears on mixing with D$_2$O; 9.68 (1H,s,CHO), 4.43 (1H,d,1'''), 4.18 (1H,d,1'), 3.46(3H,s,3'''OMe), 3.43(3H,s,2'''OMe), 2.45 (6H,s,NMe$_2$), 1.22(3H,s,12-CH$_3$);

$^{13}$C-NMR(CDCl$_3$) ppm 202.98 (d,C-20), 172.97(s,C-1), 161.63 (s,C-9), 103.98(d,C-1'), 100.33(d,C-1'''), 62.29(s,C-12), 61.73(d,C-13), 61.40(q,3'''OMe), 59.23(q,2'''OMe), 16.45(q,C-22).

EXAMPLE 8

10,11-Dihydro-12,13-epoxy-desmycosin oxime (8)

Compound 6 (1.3 g, 1.5 mmole) is dissolved in the mixture of 13 ml of acetonitrile and 26 ml of 1% trifluoroacetic acid in water and stirred at ambient temperature for 2 hours. Product isolation is performed as described in Example 7.

Yield: 1 g (81%) of the compound of identical spectral characteristics as the compound 8 from Example 7.

EXAMPLE 9

12,13-Epoxy-desmycosin oxime 20-dimethyl acetal (9)

9-Hydroxy-10,11-dihydro-12,13-epoxy-9,11-(epoxyimino)desmycosin 20-dimethyl acetal (10)

12,13-Epoxy-desmycosin 20-dimethyl acetal (2 g, 2.4 mmole) is dissolved in 16 ml of pyridine, hydroxylamine hydrochloride (1.0 g, 14.4 mmole) is added and the mixture is stirred under nitrogen stream at ambient temperature for 4 hrs. Reaction mixture is added 160 ml of water, alkalized to pH 9 with 10% NaOH and extracted with chloroform (2×80 ml). Combined extracts are dried and evaporated to dry residue. The crude product (1.76 g) is chromatographed on a silicagel column in the solvent system A.

Yield: 0.43 g (24%) of the compound 9; Rf(A) 0.38

$^1$H-NMR(DMSO) ppm 10.42(1H,s,9-NOH), disappears on mixing with D$_2$O, 6.58(1H,d,11), 6.43(1H,d,10), 4.46 (1H,d,1'''), 4.23(1H,d,1'), 3.50(3H,s,3'''OMe), 3,45(3H,s, 2'''OMe), 3,23(3H,s,20-OMe), 3.14(3H,s,20-OMe), 2.47 (6H,s,NMe$_2$);

$^{13}$C-NMR(CDCl$_3$) ppm 172.82(s,C-1), 158.86(s,C-9), 136.33(d,C-11), 115.86(d,C-10), 104.15(d,C-1'), 102.12(d, C-20), 100.58(d,C-1'''), 63.94(d,C-13), 61.43(q,3'''OMe), 59.38(s,C-12), 59.11(q,2'''OMe), 14.81 (s,C-22);

and 0.83 g (47%) of compound 10, Rf(A) 0.32

$^1$H-NMR(DMSO) ppm 4.45(1H,d,1'''), 4.22(1H,d,1'), 3.49(3H,s,3'''OMe), 3.45(3H,s,2'''OMe), 3.23(3H,s,20-OMe), 3.14(3H,s,20-OMe), 2.46(6H,s,NMe$_2$);

$^{13}$C-NMR(CDCl$_3$) ppm 170.04(s,C-1), 110.23(s,C-9), 104.08(d,C-1'), 102.51(d,C-20), 100.24(d,C-1'''), 63.37(d,C-

13), 61.44(q,3'"OMe) 60.67(s,C-12), 59.13(q,2'"OMe), 54.34(d,C-11), 15,24(s,C-22).

What we claim is:

1. 12,13-Epoxy-tylosin derivatives of the formula I

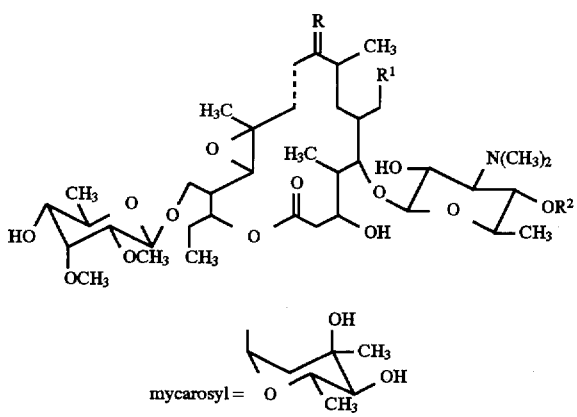

wherein R stands for O, $R^1$ stands for CHO or CH(OCH$_3$)$_2$, $R^2$ stands for H or mycarosyl, and — has the meaning of a single bond;

wherein R stands for NOH, $R^1$ stands for CHO or CH(OCH$_3$), $R^2$ stands for H or mycarosyl, and — has the meaning of a single or a double bond, and compounds of the formula II

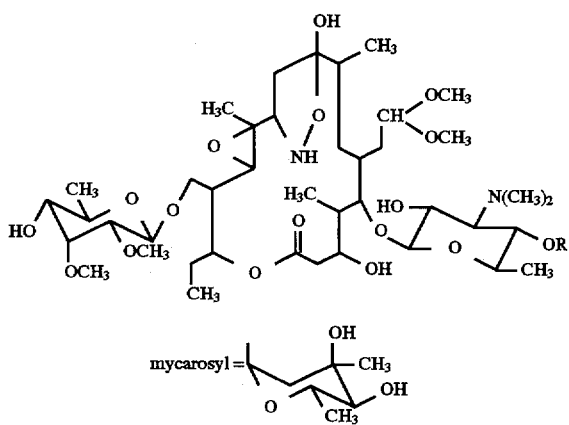

wherein R stands for H or mycarosyl.

2. The derivative of claim 1 being 10,11-Dihydro-12,13-epoxy-tylosin 20-dimethyl acetal.

3. The derivative of claim 1 being 10,11-Dihydro-12,13-epoxy-tylosin.

4. The derivative of claim 1 being 10,11-Dihydro-12,13-epoxy-desmycosin 20-dimethyl acetal.

5. The derivative of claim 1 being 10,11-Dihydro-12,13-epoxy-desmycosin.

6. The derivative of claim 1 being 10,11-Dihydro-12,13-epoxy-tylosin oxime 20-dimethyl acetal.

7. The derivative of claim 1 being 10,11-Dihydro-12,13-epoxy-desmycosin oxime 20-dimethyl acetal.

8. The derivative of claim 1 being 10,11-Dihydro-12,13-epoxy-tylosin oxime.

9. The derivative of claim 1 being 10,11-Dihydro-12,13-epoxy-desmycosin oxime.

10. The derivative of claim 1 being 12,13-Epoxy-tylosin oxime 20-dimethyl acetal.

11. The derivative of claim 1 being 12,13-Epoxy-desmycosin oxime 20-dimethyl acetal.

12. The derivative of claim 1 being 12,13-Epoxy-tylosin oxime.

13. The derivative of claim 1 being 12,13-Epoxy-desmycosin oxime.

14. The derivative of claim 1 being 9-Hydroxy-10,11-dihydro-12,13-epoxy-9,11-(epoxyimino) tylosin 20-dimethyl acetal.

15. The derivative of claim 1 being 9-Hydroxy-10,11-dihydro-12,13-epoxy-9,11-(epoxyimino)-desmycosin 20-dimethyl acetal.

16. Method for manufacture of derivative of 12,13-epoxy-tylosin of the formula I

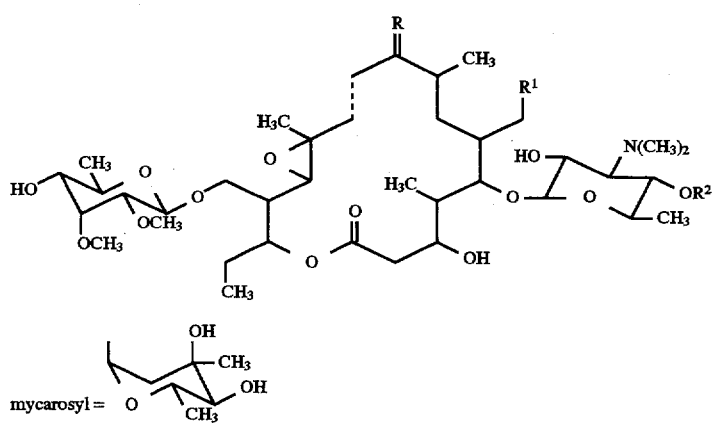

wherein R stands for O, $R^1$ stands for CHO or $CH(OCH_3)_2$, $R^2$ stands for H or mycarosyl, and — has the meaning of a single bond, wherein R stands for NOH, $R^1$ stands for CHO or $CH(OCH_3)_2$, $R^2$ stands for H or mycarosyl, and — has the meaning of a single or a double bond, and the compounds of the formula II

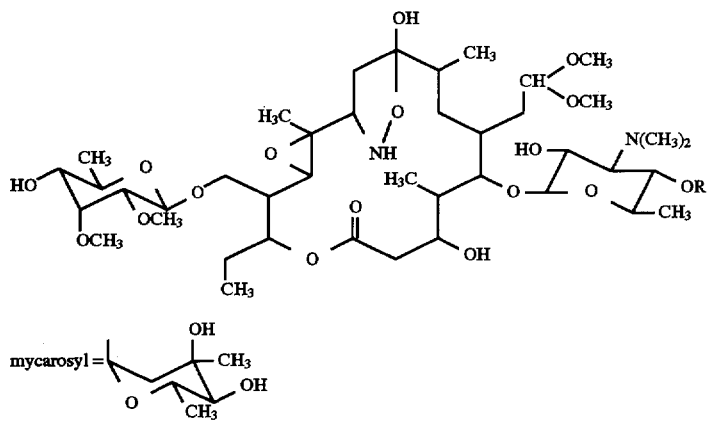

wherein R stands for H or mycarosyl
characterized in that the compound of the formula III

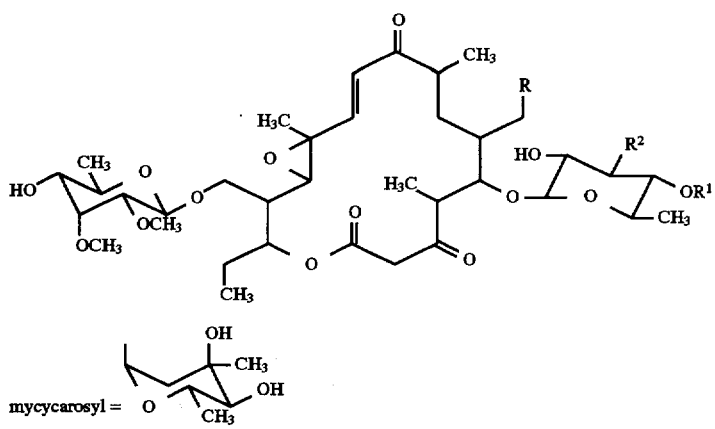

A) wherein R stands for CHO or $CH(OCH_3)_2$, $R^1$ stands for H or mycarosyl, $R^2$ stands for $N(CH_3)_2$ or $N—O(CH_3)_2$ when $R^1$ means H, is subjected to hydrogenation in an organic solvent, with 2–5% w/w palladium-on-charcoal and 0.2–0.5 MPa hydrogen pressure at ambient temperature for 5–8 hrs;

and then optionally obtained compound of the formula I, wherein R stands for O, $R^1$ stands for $CH(OCH_3)_2$, $R^2$ stands for H or mycarosyl, and — has the meaning of a single bond, is subjected to oximation with 3–6 equivalent hydroxylamine hydrochloride in pyridine, or a lower alcohol with the addition of a base such as pyridine (or $Na_2CO_3$) under nitrogen stream at ambient temperature or reflux temperature during 3–7 hrs, and then optionally to hydrolysis of acetal group;

B) wherein R stands for $CH(OCH_3)_2$, $R^1$ stands for H or mycarosyl and $R^2$ stands for $N(CH_3)_2$ is subjected to oximation as previously described and the obtained products:

the compound of the formula I, wherein R stands for NOH, $R^1$ stands for $CH(OCH_3)_2$, $R^2$ stands for H or mycarosyl, and — has the meaning of a double bond, and the compound of the formula II, wherein R stands for H or mycarosyl are chromatographically separated on a silicagel column and then optionally subjected to hydrolysis of acetal group.

17. The process of claim 16 wherein hydrolysis is performed in a mixture of acetonitrile and 0.2N HCl (1:1), or acetonitrile and 1% trifluoroacetic acid in water (1:2) at ambient temperature for 2 hrs.

18. The process of claim 16 wherein said hydrogenation is carried out in a lower $C_1$–$C_3$ aliphatic alcohol.

* * * * *